United States Patent [19]
Newell

[11] 4,220,167
[45] Sep. 2, 1980

[54] METHOD OF RESTORING NORMAL MOISTURE LEVEL TO HAIR WITH SLIGHT TO MODERATE MOISTURE DEFICIENCY

[75] Inventor: Gerald P. Newell, Hanover Park, Ill.

[73] Assignee: Helene Curtis Industries, Inc., Chicago, Ill.

[21] Appl. No.: 912,361

[22] Filed: Jun. 5, 1978

[51] Int. Cl.[2] .......................... A45D 7/04; A61K 7/06

[52] U.S. Cl. .......................................... 132/7; 424/70; 424/71

[58] Field of Search .................. 132/7, 9; 424/70, 71, 424/65, DIG. 2, 362, 365

[56] References Cited

U.S. PATENT DOCUMENTS

| | | | |
|---|---|---|---|
| 3,235,457 | 2/1966 | Laden | 424/70 X |
| 3,450,674 | 6/1969 | Walles | 424/71 |
| 3,683,939 | 8/1972 | Johnsen | 424/70 |
| 3,822,312 | 7/1974 | Sato et al. | 424/70 |
| 3,948,943 | 4/1976 | Eberhardt et al. | 424/65 |
| 4,047,537 | 9/1977 | Shaw | 132/7 |
| 4,076,800 | 2/1978 | Marsh et al. | 424/70 |
| 4,115,549 | 9/1978 | Scott | 132/7 X |

FOREIGN PATENT DOCUMENTS

| | | | |
|---|---|---|---|
| 44-22440 | 9/1969 | Japan . | |
| 49-27643 | 7/1974 | Japan | 424/70 |
| 51-20639 | 6/1976 | Japan | 424/70 |
| 7604794 | 11/1976 | Netherlands | 424/70 |

OTHER PUBLICATIONS

Cosmetics Science and Technology-Editor: Edward Sagarin, Interscience Publishers, Inc. New York 1957, pp. 383-383, 405.

American Perfumer and Cosmetics-vol. 78, No. 10 Oct. 1963 "Proteins in Cosmetics" pp. 69-72.

Drug & Cosmetic Industry 84 (4) at p. 440 and (1960) Thomsen.

*Primary Examiner*—Stuart S. Levy
*Attorney, Agent, or Firm*—Dressler, Goldsmith, Shore, Sutker & Milnamow, Ltd.

[57] ABSTRACT

A method of restoring the normal moisture level in hair initially having a slight to moderate moisture deficiency comprising the steps of: (1) shampooing the hair with a moisture stabilizing shampoo; (2) conditioning the shampooed hair with a moisture stabilizing conditioner; (3) thereafter applying a moisture control styling lotion; (4) at least once a month applying a deep heat treatment conditioner to said freshly shampooed hair; and (5) at least once a month applying a moisture gain intensive conditioner for at least 15 minutes to said hair; each of said shampoos, conditioners and lotions comprising from about 0.01 to about 1.0 weight percent of sodium-2-pyrrolidone-5-carboxylate, from about 0.1 to about 5.0 weight percent of glycerin and from about 0.01 to about 5.0 weight percent of protein derived from a collagenous source.

8 Claims, No Drawings

METHOD OF RESTORING NORMAL MOISTURE LEVEL TO HAIR WITH SLIGHT TO MODERATE MOISTURE DEFICIENCY

BACKGROUND OF THE INVENTION

This invention relates to compositions for applications to hair and more specifically relates to compositions for restoring a normal moisture level in hair initially having a slight to moderate moisture deficiency.

The use of hair coloring or bleaching products, permanents straighteners, blowdryers and exposure to sun, wind, indoor heating, etc. are all drying and damage the hair by robbing it of moisture. Moisture deficient hair is dull, brittle and lifeless.

A number of products have been developed in recent years to improve the condition of hair. While many of the available hair-conditioning compositions improve the sheen, combability and manageability of hair, they do little to restore and maintain the normal moisture content of hair. Thus there is a need for improved products which can restore and maintain the normal content of hair as well as condition it to improve its sheen, combability and the like. The present invention provides a method for achieving this result with hair initially having a slight to moderate moisture deficiency.

Laden U.S. Pat. No. 3,235,457, issued Feb. 15, 1966, discloses the use of the free acid or the hygroscopic salts of 2-pyrrolidone-5-carboxylic acid, 1-methyl-2-pyrrolidone-5-carboxylic acid and 4-methyl-2-pyrrolidone-5-carboxylic acid as humectants in cosmetic compositions which are to be applied to hair or skin. Laden discloses incorporating the humectants into the cosmetics and other compositions to prevent the products from losing moisture and drying out in storage. Laden further teaches that the humectants must be present in an amount of at least 2 weight percent of such compositions, and preferably from 4 to 10 weight percent. Glycerin is also known to be a humectant.

It has now surprisingly been found that when from about 0.01 to about 1 weight percent of sodium-2-pyrrolidone-5-carboxylate is incorporated into hair treatment compositions such as shampoos, conditioners, and the like, along with glycerin and protein derived from a collagenous source and such compositions are used in concert with each other in a prescribed manner, the moisture level can be restored to slightly to moderately moisture deficient hair.

Thus the present invention provides an improved process for restoring the normal moisture level in slight to moderately moisture deficient hair.

SUMMARY OF THE INVENTION

The present invention provides a method of restoring the normal moisture level to slight to moderately moisture deficient hair comprising the steps of: (1) shampooing the hair with a moisture stabilizing shampoo; (2) conditioning the hair after each shampooing with a moisture stabilizing conditioner; (3) thereafter applying a moisture control styling lotion to the shampooed, conditioned hair; (4) at least once a month applying a deep heat treatment conditionerto said freshly shampooed hair; and (5) at least once a month, applying a moisture gain intensive conditioner for at least 15 minutes to freshly shampooed hair.

The compositions used in the practice of this invention, i.e., shampoos, styling compositions and conditioners each contain from about 0.01 to about 1.0 weight percent of sodium-2-pyrrolidone-5-carboxylate, from about 0.01 to about 5.0 weight percent of glycerin and from about 0.01 to about 5 weight percent of protein derived from collagenous sources, in addition to the generally used ingredients of such compositions. Hereinafter, the unique combination of the three ingredients will be referred to as the two humectants and protein.

The term "moisture stabilizing shampoo" refers to a shampoo containing the above two humectants and protein.

The term "moisture stabilizing conditioner" refers to a conditioner containing the combination of two humectants and protein which is applied to the hair after shampooing and then immediately rinsed from the hair.

The term "moisture control styling composition" refers to styling conditioners which can either be smoothed on prior to the hair being set or if the hair is to be blown dried to blow dry compositions as set forth hereinbelow, both of which contain the two humectants and protein.

The term "moisture gain intensive conditioner" refers to a conditioner containing the two humectants and protein which is applied to the hair for at least 15 minutes after shampooing and thereafter rinsed from the hair.

The term "moisture stabilizing night supplement gel" refers to a gel containing the two humectants and protein which is applied in small amounts and worked through the hair prior to bedtime, and allowed to stay on throughout the night to additionally moisturize the hair.

The term "moisture gain deep heat conditioner" refers to a conditioner containing the two humectants and protein which is applied to the hair and then heat applied for at least 15 and preferably 30 minutes.

In addition to the unique combination of the sodium-2-pyrrolidone-5-carboxylate, glycerin and protein in the compositions which are used in the practice of this invention, the compositions may additionally comprise quaternary conditioners, detergents, thickeners, fatty esters, non-quaternary conditioning agents, fragrance, fragrance solubilizers and the like as is common in such compositions.

DETAILED DESCRIPTION OF THE PREFERRED EMBODIMENTS

The present invention provides a method of restoring the normal moisture level to slight to moderately moisture deficient hair comprising the steps of: (1) shampooing the hair with a moisture stabilizing shampoo; (2) conditioning the hair after each shampooing with a moisture stabilizing conditioner; (3) thereafter applying a moisture control styling lotion to the shampooed, conditioned hair; and (4) at least once a month, applying a moisture gain intensive conditioner for at least 15 minutes to freshly shampooed hair, each of said shampoos, styling lotions and conditioners comprising from about 0.01 to about 1 weight percent, preferably from about 0.1 to about 1 weight percent of sodium-2-pyrrolidone-5-carboxylate; from about 0.1 to about 5.0 weight percent, preferably from about 0.5 to about 2 weight percent of glycerin and from about 0.1 to about 2.5 weight percent of protein derived from a collagenous source, and preferably from about 0.5 to about 2 weight percent of the protein.

In addition, the hair can be treated at least once a week and preferably up to three times a week with a moisture stabilizing night supplement conditioner which is applied to the hair before retiring and left on over night. The present method can additionally comprise the application of a deep heat treatment conditioner once a month, each of the conditioners containing the two humectants and protein.

In the practice of this invention, hair is preferably shampooed at least once a week and ideally at least one to three times a week, so that the conditioning process is routinely utilized.

In order to determine whether hair is slightly or moderately moisture deficient, the hair to be treated is dried out in a vacuum oven and accurately weighed. The hair is then allowed to equilibrate at an ambient room humidity and reweighed accurately. The increased weight is due to moisture pickup. The percent moisture regain is then calculated as follows:

$$\frac{\text{Wt. of hair at a given room humidity} - \text{Wt. of dry hair}}{\text{Wt. of dry hair}} \times 100 = \%$$

The average results for normal hair is approximately 6.3. Moderately moisture deficient hair regains an average of 5.6 percent moisture. Severely moisture deficient hair regains approximately 5.0 weight percent or less.

Depending upon whether the compositions used in the practice of this invention are formulated as shampoos or as various types of conditioners or setting lotions, the compositions used in this invention can include other ingredients which are generally used in the particular type of compositions. Thus, for example, if the composition is formulated as a shampoo, it can include from about 5 to about 50% by weight of a suitable detergent such as sodium lauryl sulfate or a sodium lauryl sulfate containing detergent, i.e., Dynol SAM detergent sold by Richardson Co., alone or together with an amphoteric surface active agent such as the mono-sodium salt of N-lauryl-iminodipropionic acid, i.e., Deriphat 160C sold by General Mills, which can be present in the shampoo in an amount of from about 0.05 to 10 weight percent, preferably 0.1 to about 5 weight percent of the shampoo, and a nonionic detergent such as coconut diethanolamide, i.e., Ninol 2012 sold by Stepan Chemical Company. In addition, the shampoo can include foam boosters and stabilizers such as AMMONYX-LO lauryl dimethylamine oxide sold by Onyx Chemicals and which can be present in an amount of from about 1 to 15 weight, preferably from about 2 to 10 weight percent of the composition. The shampoos can also include chelating agents such as ethylenediaminetetraacetic acid (EDTA), preservatives such as Methyl Parasept sold by Tenneco Chemical Company, glutaraldehyde, monomethyloldimethyl hydantoin and the like. The shampoo formulations can also include perfuming agents, coloring agents and the like.

The conditioning compositions of this invention can include, in addition to the sodium-2-pyrrolidone-5-carboxylate, glycerin and protein, conditioners such as alkylmethyl bis (polyoxyethylene) quaternary ammonium salt, i.e., Ethoquad 0/12 sold by Armak Chemical Company, which can be present in an amount of from about 0.5 to about 5 weight percent, preferably from about 2 to about 4 weight percent; a cationic surface active agent such as cetyltrimethyl ammonium chloride (29% active solution sold under the trademark Barquat CT-429 sold by by Lonza, Inc.; stearic acid, which can be present in an amount of from about 0.5 to about 3 weight percent, preferably 1.0 to 2.0 weight percent; glycerol monostearate which can be present in an amount of from about 0.5 to about 5 weight percent, preferably from about 2.0 to about 3 weight percent, preferably from about 1 to about 2 weight percent, cetyl alcohol which can be present in an amount of about 0.5 to about 5 weight percent, preferably from about 2.0 to about 3 weight percent; polyethylene glycol polymer of ethyleneoxide having an average molecular weight of 3,000–3,700 such as that sold by Union Carbide Chemical Company under the tradename Carbowax 4000 which can also be present in an amount of 0.5–5.0 weight percent, and pantothenyl alcohol which can be present in an amount of 0.05 to 5 weight percent of the composition, in addition to perfuming agents, coloring agents and the like.

It will be understood to those skilled in the art that the above ingredients variously serve as conditioning agents, thickeners and opacifiers, anti-static agents and the like. Generally speaking, when the unique combination of humectants and protein are combined with any or all of the above ingredients, the resulting conditioner is referred to herein as a moisture stabilizing conditioner.

If a moisture control setting conditioner is desired, the three principal ingredients can, for example, be combined with denatured ethanol such as SD alcohol 40, generally at about 25 to 35 weight percent of the composition; from about 1 to about 10 weight percent of a film forming resin such as the 80% vinylpyrrolidone-20% dimethylaminoethyl methacrylate copolymer quaternized with diethyl ammonium sulfate such as GAF Quat 734 sold by General Anilne and Film Corporation; from 0.1 to about 2 weight percent of a quaternary anti-static conditioner such as dimethyl difatty ammonium chloride in aqueous isopropanol such as that sold by Ashland Chemical Company under the tradename ADOGEN 432 CG, and a cationic surface active agent such as Ethoquad 0/12. The moisture control setting conditioner can additionally include perfumes and perfume solubilizers such as a polyoxyalkylene derivative of sorbitan monolaurate, i.e., TWEEN 20, sold by ICI United States Inc., and coloring agents.

If the hair is to be blown dry or set with hot curlers, a thermal styling protective lotion is provided by combining the protein and 2 humectants with from about 0.2 to about 10 weight percent, preferably from about 0.5 to about 5 weight percent of, for example, polyvinylpyrrolidone (PVP 30) sold by GAF Corporation, a quaternary conditioner such as a polymer of hydroxyethylcellulose reacted with epichlorihydrin and quaternized with trimethylamine, i.e., Polymer JR 400, sold by Union Carbide Corporation, and an anti-static conditioner with 5 percent propylene glycol as a stabilizer such as oleyldimethyl benzyl ammonium chloride sold under the tradename AMMONYX KP by Onyx Chemicals. The thermal styling lotion can additionally include perfuming agents and the like.

In addition to the moisture stabilizing conditioner, moderate to slight moisture deficient hair can additionally be benefited by the use of a supplement gel conditioner which is applied to the hair at night about 3 times a week and which can be formulated in gel form by, for example, incorporating the humectants and protein in an aqueous solution containing from about 0.1 to about 2 weight percent of a water soluble high molecular weight carboxy vinyl polymer such as Carbopol 940 sold by B. F. Goodrich Chemicals Company and from about 20 to about 30 weight percent of, for example, ethyl alcohol denatured with brucine sulfate such as 200 proof SD alcohol 40.

Moderate moisture deficient hair can additionally be benefited by a deep heat treatment conditioner which is applied to the hair once a month in the case of moderate moisture deficiency. The deep heat treatment compositions, in addition to the humectants and protein, contain additional conditioners such as Barquat CT-429, generally employed in amounts of from about 0.5 to about 5 weight percent of the compositions, cetyl alcohol polyethylene glycol high molecular weight ether complex such as Promulgen D which generally is present in an amount of from about 0.5 to about 5 weight percent, from about 0.5 to about 10 weight percent of mineral oil, from about 0.5 to about 10 weight percent of isopropyl myristate, from about 0.5 to about 10 weight percent of cetyl alcohol and from about 0.5 to about 10 weight percent of ethylene glycol monostearate.

An alternate intensive conditioner for slight to moderate moisture deficient hair can, in addition to the humectants and protein, include various hair conditioners such as an aqueous cationic surface active agent such as cetyltrimethyl ammonium chloride, i.e., BARQUAT CT-429 sold by Lonza, Inc. in an amount of from about 0.5 to about 5 weight percent of the compositions, from about 0.5 to about 5.0 weight percent of an acid stabilized glycerol monostearate, i.e., Lexemul AR sold by Inolex Corporation, from about 0.5 to about 5.0 weight percent of a high molecular weight cetyl alcohol-polyethylene glycol ether complex, i.e., Promulgen D sold by Robinson-Wagner Co., from about 0.5 to about 10 weight percent of mineral oil, preferably 65 to 75 weight, from about 0.5 to about 10 weight percent of isopropyl myristate, from about 0.5 to about 10 weight percent of a thickener such as cetyl alcohol and from about 0.5 to about 10 weight percent of ethylene glycol monostearate, i.e., Product EG-19 sold by Clintwood Chemical Company.

A moisture conditioner hair spray composition can also be used in the practice of the present invention by incorporating from about 1 to about 15 percent by weight of a water soluble resin consisting of 60% vinylpyrrolidone-40% vinylacetate copolymer, i.e. PVP/VA-E-635, sold by General Aniline and Film Corporation, from about 0.05 to about 1.5 percent by weight of a copolymer of dimethyl polysiloxane and a polyoxyalkylene ester such as Silicone Fluid SF-1066 sold by General Electric and from about 40 to about 80 weight percent of alcohol, i.e., SD Alcohol 40.

The preferred proteins are water or alcohol soluble polypeptides derived from collagenous sources such as those sold under the tradenames Lexein X250 and WSP-A200 Protein by Inolex Corporation.

The following compositions are illustrative of those which can be used in the practice of this invention.

EXAMPLE 1

Moisture Stabilizing Shampoo

A moisture stabilizing shampoo composition is formulated using the following ingredients:

| Ingredient | Weight Percent |
|---|---|
| Sodium DL-2-pyrrolidone-5-carboxylate (50% aqueous soln.) | 0.10 |
| Glycerin | 0.10 |
| Protein | 0.10 |
| Dynol SAM | 42.00 |
| Ninol 2012 | 1.00 |
| Lauryl dimethylamine oxide | 2.00 |
| Deriphat 160C | 0.10 |
| Water | to 100 percent |

In addition, the above shampoo composition also includes preservatives, chelating agents, coloring agents, perfume and the like. The following example illustrates such a composition.

EXAMPLE 2

Moisture Stabilizing Shampoo

| Ingredient | Weight Percent |
|---|---|
| Sodium DL-2-pyrrolidone-5-carboxylate (50% aqueous soln.) | 0.01 |
| Glycerin | 0.10 |
| Protein | 0.10 |
| Dynol SAM | 42.000 |
| Ninol 2012 | 1.000 |
| Lauryl dimethylamine oxide | 2.000 |
| Deriphat 160C | 0.100 |
| Water | to 100 percent |
| Methyl Parasept | 0.150 |
| Versene Flakes | 0.100 |
| Citric acid | 0.190 |
| Monomethylol dimethyl hydantoin | 0.100 |
| Perfume | 0.300 |
| Coloring agent | 0.015 |
| Ammonium chloride | 0.600 |

EXAMPLE 3

Moisture Stabilizing Conditioner

A moisture stabilizing conditioner is formulated using the following ingredients:

| Ingredient | Weight Percent |
|---|---|
| Sodium DL-2-pyrrolidone-5-carboxylate (50% aqueous soln.) | 0.25 |
| Glycerin | 0.10 |
| Protein | 0.20 |
| Ethoquad 0/12 | 2.50 |
| Carbowax 4000 | 1.50 |
| Stearic acid | 1.50 |
| Glycerol monostearate | 1.50 |
| Cetyl alcohol | 2.50 |
| DL-pantothenyl alcohol | 0.10 |
| Anti-foam agent | 0.20 |
| Preservative | 0.10 |
| Coloring agent | 0.30 |
| Water | to 100 |

EXAMPLE 4

Moisture Control Setting Conditioner

A moisture control setting conditioner composition is formulated using the following ingredients:

| Ingredient | Weight Percent |
|---|---|
| Sodium DL-2-pyrrolidone-5-carboxylate (50% aqueous soln.) | 0.500 |
| Glycerin | 1.000 |
| Protein | 1.000 |
| GAF Quat 734 (50% of soln.) | 5.000 |
| Adogen 432 CG | 0.125 |
| Ethoquad 0/12 | 0.375 |

-continued

| Ingredient | Weight Percent |
|---|---|
| SD Alcohol | 30.000 |
| Tween 20 | 0.500 |
| Water | to 100 |

The setting conditioner can additionally comprise perfuming agents, coloring agents and the like.

EXAMPLE 5

Thermal Styling Protective Lotion

A blow-dry conditioning and protective lotion composition is formulated with the following ingredients:

| Ingredient | Weight Percent |
|---|---|
| Sodium-DL-2-pyrrolidone-5-carboxylate | 0.10 |
| Glycerin | 0.10 |
| Lexein X250 | 1.00 |
| PVP 30 | 1.00 |
| Oleyl dimethylbenzyl ammonium chloride | 0.50 |
| Water | to 100.0 |

The blow-dry composition can additionally include perfuming agents, preservatives and the like.

EXAMPLE 6

Supplemental Gel Conditioner

A supplemental gel conditioner which is used to help to restore moisture to moisture deficient hair is formulated using the following ingredients:

| Ingredient | Weight Percent |
|---|---|
| Sodium-DL-2-pyrrolidone-5-carboxylate (50% aqueous soln.) | 2.00 |
| Glycerin | 1.50 |
| Lexein X250 (protein) | 0.50 |
| Carbopol 940 | 0.35 |
| SD Alcohol 40 | 25.00 |
| Non-ionic surfactant | 0.5 |
| Perfuming agent | 0.1 |
| Water | 100.0 |

The supplemental gel conditioner is used three times a week.

EXAMPLE 7

Deep Heat Treatment Conditioner

A deep heat treatment conditioner which is used to help restore moisture to slight to moderate moisture deficient hair is formulated using the following ingredients.

| Ingredient | Weight Percent |
|---|---|
| Sodium-DL-2-pyrrolidone-5-carboxylate (50% aqueous soln.) | 5.0 |
| Glycerin | 5.0 |
| Protein | 2.5 |
| Barquat CT-429 | 4.3 |
| DL-panthothenyl alcohol | 0.1 |
| Acid stabilized glycerol monostearate | 1.0 |
| Promulgen D | 1.0 |
| MIneral oil 65/75 | 2.0 |
| Isopropyl myristate | 2.0 |
| Cetyl alcohol | 3.5 |
| Ethylene glycol monostearate | 2.0 |
| Perfume | 0.4 |

-continued

| Ingredient | Weight Percent |
|---|---|
| Coloring | 0.2 |
| Water | to 100.0 |

The deep heat treatment composition is used once a month on hair having a slight to moderate moisture deficiency, and is preferably applied in a beauty salon to freshly shampooed hair.

EXAMPLE 8

Intensive Conditioner for Damaged Hair

An intensive conditioner composition is formulated using the following ingredients:

| Ingredient | Weight Percent |
|---|---|
| Sodium-DL-2-pyrrolidone-5-carboxylate (50% aqueous soln.) | 4.00 |
| Glycerin | 3.00 |
| Protein | 4.00 |
| Barquat CT-429 | 4.3 |
| Acid stabilized glycerol monostearate | 1.0 |
| Promulgen D | 1.0 |
| Mineral oil 65/75 | 2.0 |
| Isopropyl myristate | 2.0 |
| Cetyl alcohol | 3.5 |
| Ethylene glycol monostearate | 2.0 |
| Perfume | 0.4 |
| Preservative | 0.2 |
| Water | to 100 |

EXAMPLE 9

Moisture Control Hair Spray Composition

A moisture control hair spray composition is formulated from the following ingredients:

| Ingredients | Weight Percent |
|---|---|
| Sodium-DL-2-pyrrolidone-5-carboxylate (50% aqueous soln.) | 0.1 |
| Glycerin | 0.1 |
| Alcohol soluble protein | 0.1 |
| PVP/VA-E-635(50%) | 10.0 |
| Silicone Fluid SF-1066 | 0.2 |
| Citric acid | 0.3 |
| Perfume | 0.3 |
| SD 40 alcohol | 78.6 |
| Water | to 100.0 |

It is to be understood that the foregoing examples are intended to be merely illustrative and that modifications and variations will be apparent to those skilled in the art.

I claim:

1. A method for restoring normal moisture level to slight to moderately moisture deficient hair comprising the steps of:

(1) shampooing the hair with a moisture stabilizing shampoo;

(2) conditioning the shampooed hair with a moisture stabilizing composition;

(3) thereafter applying a moisture control styling lotion; and (4) at least once a month applying a moisture gain intensive conditioner for at least 15 minutes to said hair;

each of said shampoos, conditioners and lotions comprising from about 0.01 to about 1.0 weight percent of sodium-2-pyrrolidone-5-carboxylate, from about 0.01 to about 5.0 weight percent of glycerin and from about 0.01 to about 5.0 weight percent of protein derived from a collagenous source.

2. The method of claim 1 additionally comprising the step of applying a moisture stabilizing night supplement gel to said hair at least once a week, said gel comprising from about 0.01 to about 1.0 weight percent of sodium-2-pyrrolidone-5-carboxylate, from about 0.01 to about 5.0 weight percent of glycerin and from about 0.01 to about 5.0 weight percent of protein derived from a collagenous source.

3. The method of claim 2 wherein said gel is applied to the hair twice a week.

4. The method of claim 2 wherein said gel is applied to the hair twice a week.

5. The method of claim 4, additionally comprising the step of at least once a month applying a deep heat treatment conditioner to said moisture deficient hair, said conditioner comprising from about 0.01 to about 1.0 weight percent of sodium-2-pyrrolidone-5-carboxylate, from about 0.01 to about 5.0 weight percent of glycerin and from about 0.01 to about 5.0 weight percent of protein derived from a collagenous source.

6. The method of claim 4 wherein said gel is applied to the hair three times a week.

7. The method of claim 6, additionally comprising the step of at least once a month applying a deep heat treatment conditioner to said moisture deficient hair, said conditioner comprising from about 0.01 to about 1.0 weight percent of sodium-2-pyrrolidone-5-carboxylate, from about 0.01 to about 5.0 weight percent of glycerin and from about 0.01 to about 5.0 weight percent of protein derived from a collagenous source.

8. The method of claim 1, additionally comprising the step of at least once a month applying a deep heat treatment conditioner to said moisture deficient hair, said conditioner comprising from about 0.01 to about 1.0 weight percent of sodium-2-pyrrolidone-5-carboxylate, from about 0.01 to about 5.0 weight percent of glycerin and from about 0.01 to about 5.0 weight percent of protein derived from a collagenous source.

* * * * *

UNITED STATES PATENT AND TRADEMARK OFFICE

CERTIFICATE OF CORRECTION

PATENT NO. : 4,220,167

DATED : September 2, 1980

INVENTOR(S) : Gerald P. Newell

It is certified that error appears in the above—identified patent and that said Letters Patent is hereby corrected as shown below:

In the list of References Cited under Other Publications, in the right-hand column in the page citation for the second publication listed (Sagarin) "383-383" should be --382-383--.

Column 1, line 62, there should be a space between "conditioner" and "to".

Column 3, line 12, "treated" should be --tested--.

Signed and Sealed this

*Second* Day of *December 1980*

[SEAL]

*Attest:*

SIDNEY A. DIAMOND

*Attesting Officer* *Commissioner of Patents and Trademarks*